United States Patent [19]
Iwamoto et al.

[11] Patent Number: 5,939,610
[45] Date of Patent: Aug. 17, 1999

[54] ION CONCENTRATION MEASURING APPARATUS WITH INTERNAL CALIBRATION FLUID RESERVOIR

[75] Inventors: Yasukazu Iwamoto; Hiromi Ohkawa, both of Miyanohigashi-machi, Japan

[73] Assignee: Horiba, Ltd., Kyoto, Japan

[21] Appl. No.: 08/676,429

[22] Filed: Jul. 8, 1996

[30] Foreign Application Priority Data

Jul. 8, 1995 [JP] Japan ................................... 7-196209

[51] Int. Cl.[6] .................................................. G01N 27/36
[52] U.S. Cl. ......................... 73/1.03; 73/1.01; 204/416; 204/420
[58] Field of Search ........................... 73/1 R, 1.01, 1.88, 73/1.02, 1.03; 204/416–420; 324/438

[56] References Cited

U.S. PATENT DOCUMENTS

| | | | |
|---|---|---|---|
| 3,625,850 | 12/1971 | Arrington | 204/416 |
| 4,016,866 | 4/1977 | Lawton | 600/348 |
| 4,260,950 | 4/1981 | Hadden et al. | 73/1 R |
| 4,473,458 | 9/1984 | Schwartz et al. | 73/1 R |
| 5,124,659 | 6/1992 | Frola et al. | |
| 5,511,408 | 4/1996 | Yoshioka et al. | |

FOREIGN PATENT DOCUMENTS 0372121 of 0000 European Pat. Off. .

*Primary Examiner*—Hezron Williams
*Assistant Examiner*—Nashmiya Fayyaz
*Attorney, Agent, or Firm*—Price Gess & Ubell

[57] ABSTRACT

An ion concentration measuring apparatus having a housing member with a measuring electrode assembly movably mounted within the housing member is provided. A calibration fluid reservoir is also mounted within the housing member. The measuring electrode assembly can be extended for a measuring mode of operation of retracted within the housing member and appropriately sealed so that it will contact the calibration fluid for a calibration operation.

6 Claims, 6 Drawing Sheets

FIG. 2A
FIG. 2B
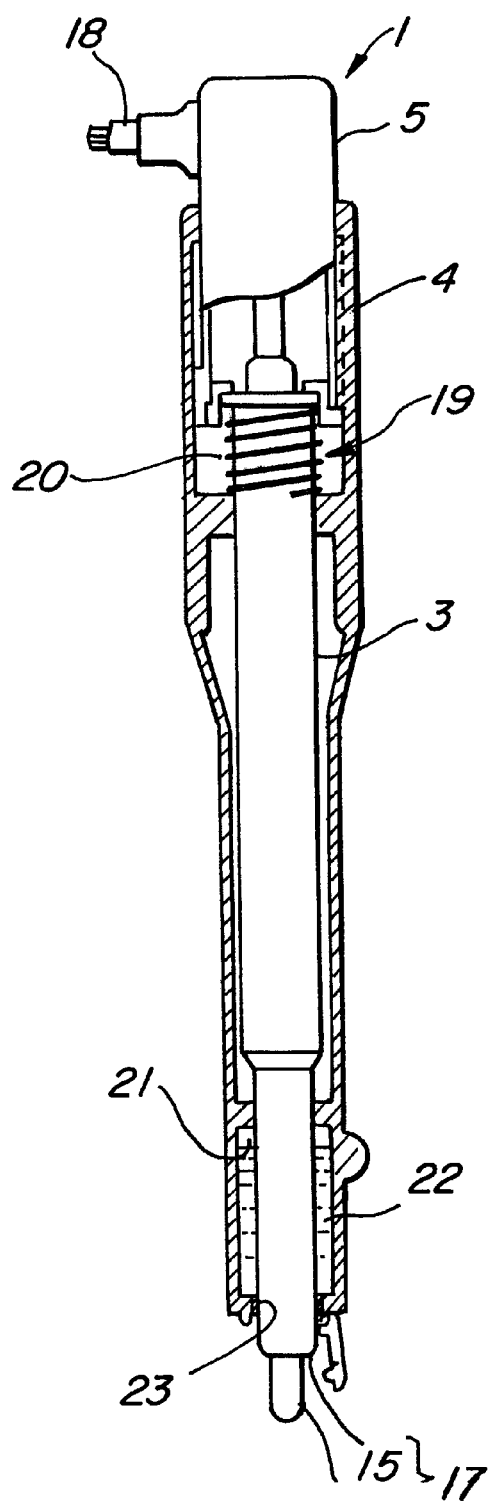
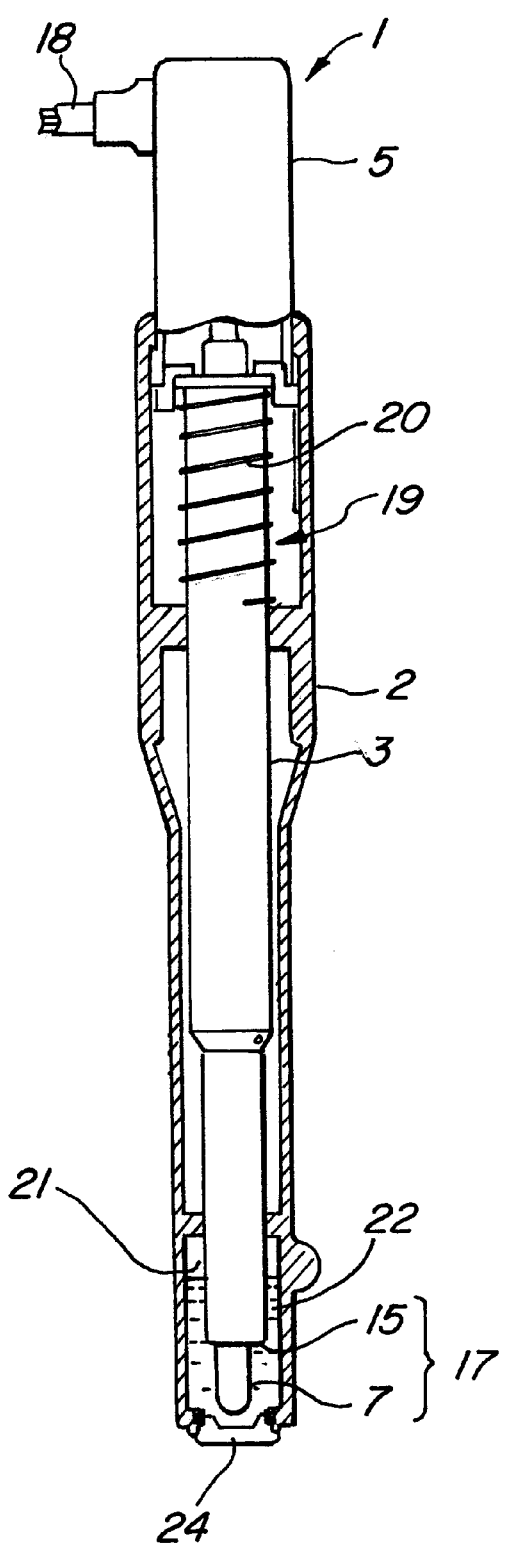

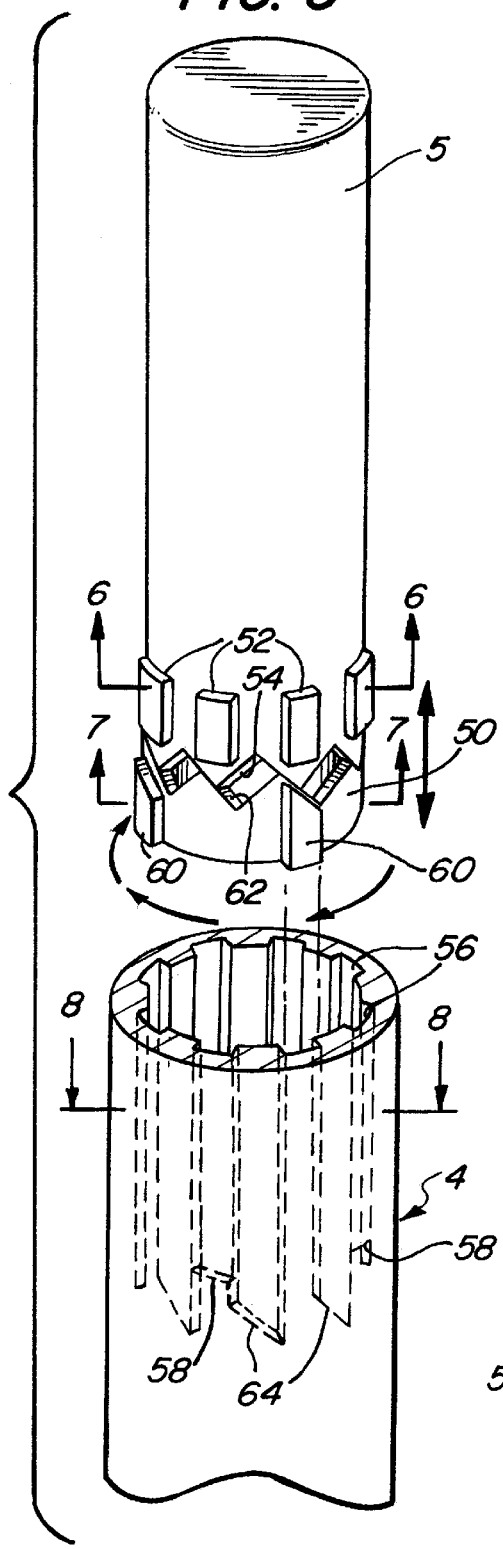
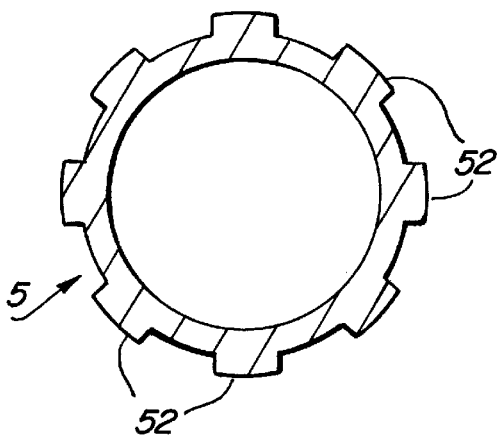
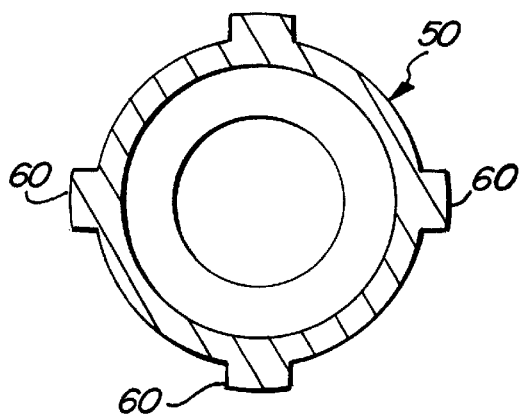
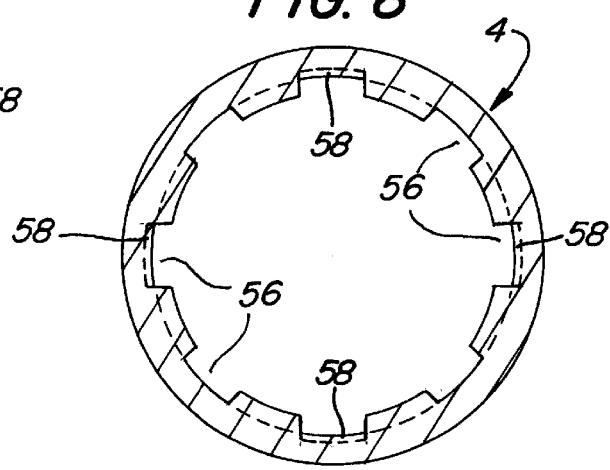

FIG. 9
FIG. 10
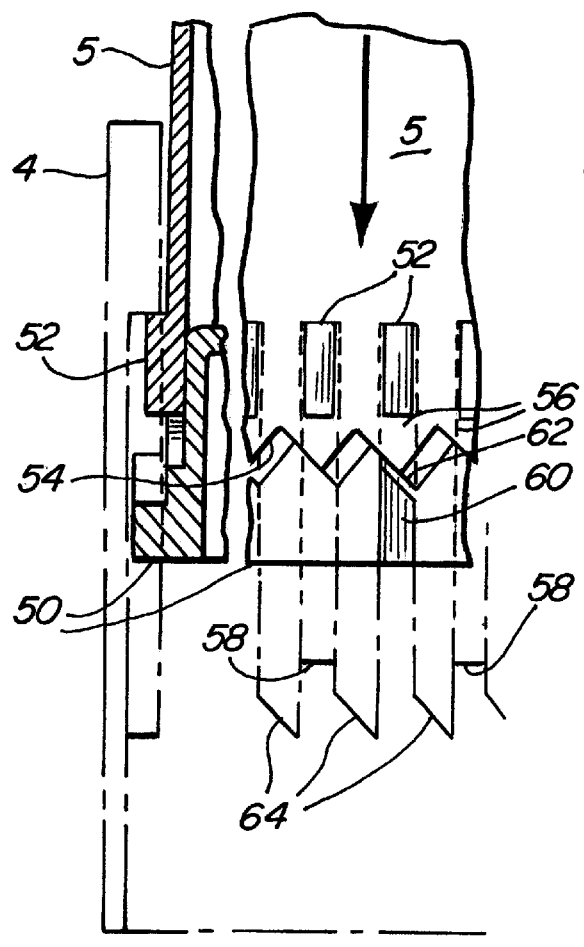
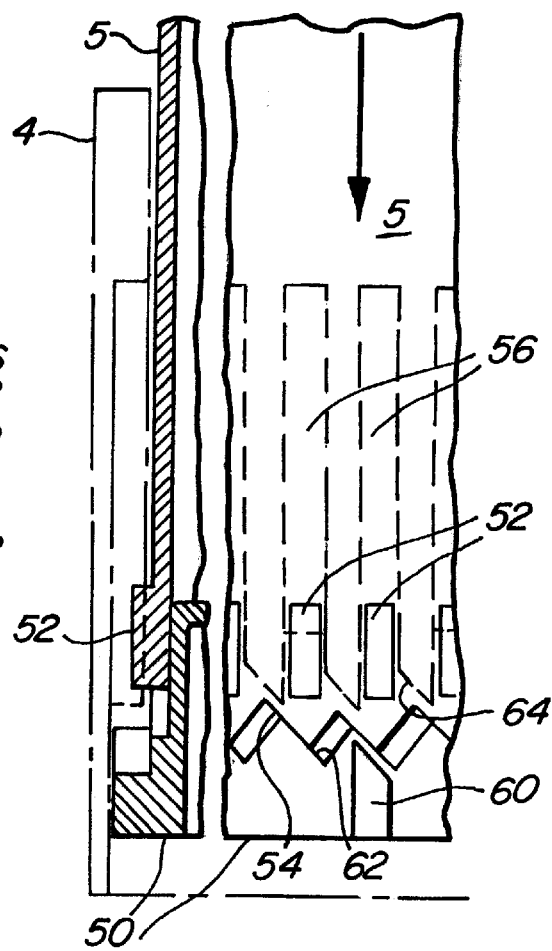

ION CONCENTRATION MEASURING APPARATUS WITH INTERNAL CALIBRATION FLUID RESERVOIR

BACKGROUND OF THE INVENTION

1. Field of the Invention

This invention relates to an improvement in an apparatus for measuring ion concentrations such as pH, calcium ion, potassium ion, etc. and, more particularly, to apparatus for providing an efficient calibration of the measuring instrument.

2. Description of Related Art

As examples of a pH meter for measuring the pH of a solution, reference can be made to FIG. 4, wherein a plastic body main part has a measuring portion 42 comprising an ion responding portion of a measuring electrode and a reference electrode liquid junction at the tip end. A plastic protection cap 43 can be removably attached and can hold a calibration liquid which is used for calibrating the pH meter. A ring assembly 44 can be used to protect the measuring portion 42 when the protection cap 43 is removed.

The conventional pH meter disclosed in FIG. 4 has an advantage in that attaching the protection cap 43 to the measuring portion 42 can not only protect the measuring portion 42 during storage, but it can also provide calibration fluid to the measuring portion during the storage nonmeasuring period.

The protection cap 43 is constructed separately from the body 41 of the pH meter and, thus, a disadvantage occurs in operation in the field in that the cap can be easily lost, requiring measures to ensure that the cap is not lost to the detriment of the instrument. When the measuring portion 42 is to be calibrated just prior to a measurement, the removed protection cap 43 must be attached to the top end of the body 41, which sometimes renders the operation troublesome to the field operator.

An example of a pH and specific ion concentration measuring instrument can be seen in U.S. Pat. No. 5,124,659. U.S. Pat. No. 5,511,408 discloses an automatic calibrating apparatus wherein calibration can be accomplished when the sensor member is inserted into a chamber during a storage mode of operation. The art is still seeking to improve ion concentration measuring apparatus.

OBJECTS AND SUMMARY OF THE INVENTION

The present invention provides an ion concentration measuring apparatus which can not only reliable protect the measuring portion of the instrument during a nonmeasuring period or storage mode, but can also automatically calibrate the measuring portion in a storage mode. The measuring instrument can be quickly changed over from a measuring state to a nonmeasuring state and vice versa, thereby enabling both an easy calibration and use by an operator. The ion concentration measuring apparatus is constructed to have a measuring electrode assembly which includes an ion responding portion and a reference electrode liquid junction that is movably mounted in an axial direction within a housing member. The electrode assembly can be operated with literally the touch of the finger of an operator so that it can move back and forth to extend from the housing member in an operating mode and be retracted within the housing member in a storage and calibration mode. A retraction mechanism is mounted within a cylindrical body of the housing member at a top end, while a calibration liquid can be sealingly stored between the interior of the housing body and the measuring electrode assembly. The measuring electrode assembly member is extended for a measurement cycle and is then retracted into the housing body to thereby create an immersion of the measuring electrode assembly in a calibration liquid to enable an easy calibration procedure to take place.

As can be appreciated, in the storage or calibration mode, the measuring electrode assembly is retracted into the housing member body. Consequently, the ion responding portion of the measuring electrode assembly is protected. At the same time, the ion responding portion is immersed in the calibration liquid, which can be stored within the housing body, to thereby enable an automatic calibration. The operator, by manipulating the retraction mechanism, can protrude the measuring electrode assembly to the outside of the housing body. The specific ion concentration measurement can be carried out by immersing the electrode assembly in the sample liquid to be measured. If it is desired to ensure the proper calibration of the measuring electrode assembly, a simple manipulation of a control member for the retraction mechanism can immediately immerse the measuring electrode assembly in the calibration liquid within the housing member, and the desired calibration can be achieved.

The ion concentration measuring apparatus of the present invention includes a hollow elongated housing member that is configured to be hand-held by an operator, with an upper opening and a lower opening. An elongated electrode measuring member having, at a lower end, a measuring electrode and a reference electrode, is movably mounted within the housing member. A retraction mechanism for movably mounting the electrode measuring member can include a control member and a spring assembly that can bias the electrode measuring member towards an extension position from the lower end of the housing member. The control member will have a predetermined range of movement and will extend upward from an upper opening in the housing member. The control member is operatively connected to the elongated electrode measuring member so that it will move axially with the elongated electrode measuring member. When the control member is retracted into the housing member, it can releasably hold the electrode measuring member in an operating position exterior of the housing member. A subsequent release of the control member will permit the spring assembly to retract the electrode measuring member into a storage position within the lower end of the housing member. The lower end of the housing member includes a liquid reservoir and a sealing structure to maintain a calibration fluid internally within the housing member and to operatively apply it to the electrode measuring member to enable a calibration of the instrument. The sealing structure can include a pivotable sealing member in one embodiment or, alternatively, can provide an annular sealing ring with a protective rubber cap position at the end of the measuring electrode assembly.

BRIEF DESCRIPTION OF THE DRAWINGS

The objects and features of the present invention, which are believed to be novel, are set forth with particularity in the appended claims. The present invention, both as to its organization and manner of operation, together with further objects and advantages, may best be understood by reference to the following description, taken in connection with the accompanying drawings.

FIG. 2a is a schematic representation illustrating the operation of the ion concentration measuring apparatus in an extended measuring mode;

FIG. 2b is a schematic representation illustration the operation of the ion concentration measuring apparatus in a storing and/or calibration mode;

FIG. 5 is a perspective exploded view of retention mechanism;

FIG. 6 is a cross-sectional view of a portion of the control member 5;

FIG. 7 is cross-sectional view of the locking member 50;

FIG. 8 is a cross-sectional view of the sealing cap 4;

FIG. 9 is a partial cross-sectional view of an extension movement of the retention mechanism;

FIG. 10 is a partial cross-sectional view of the retention mechanism rotating the locking member 50;

DETAILED DESCRIPTION OF THE PREFERRED EMBODIMENTS

The following description is provided to enable any person skilled in the art to make and use the invention and sets forth the best modes contemplated by the inventors of carrying out their invention. Various modifications, however, will remain readily apparent to those skilled in the art, since the general principles of the present invention have been defined herein specifically to provide a hand-held ion concentration measuring apparatus with an internal calibration fluid reservoir.

The specific operation of an ion concentration measuring apparatus such as a pH meter, etc. is known by those skilled in the field, including the manner in which the measuring electrode and the reference electrode generate electrical signals that can be processed to measure a characteristic of the sample being investigated. Accordingly, these features of the present invention are omitted from the description.

Figure 1:
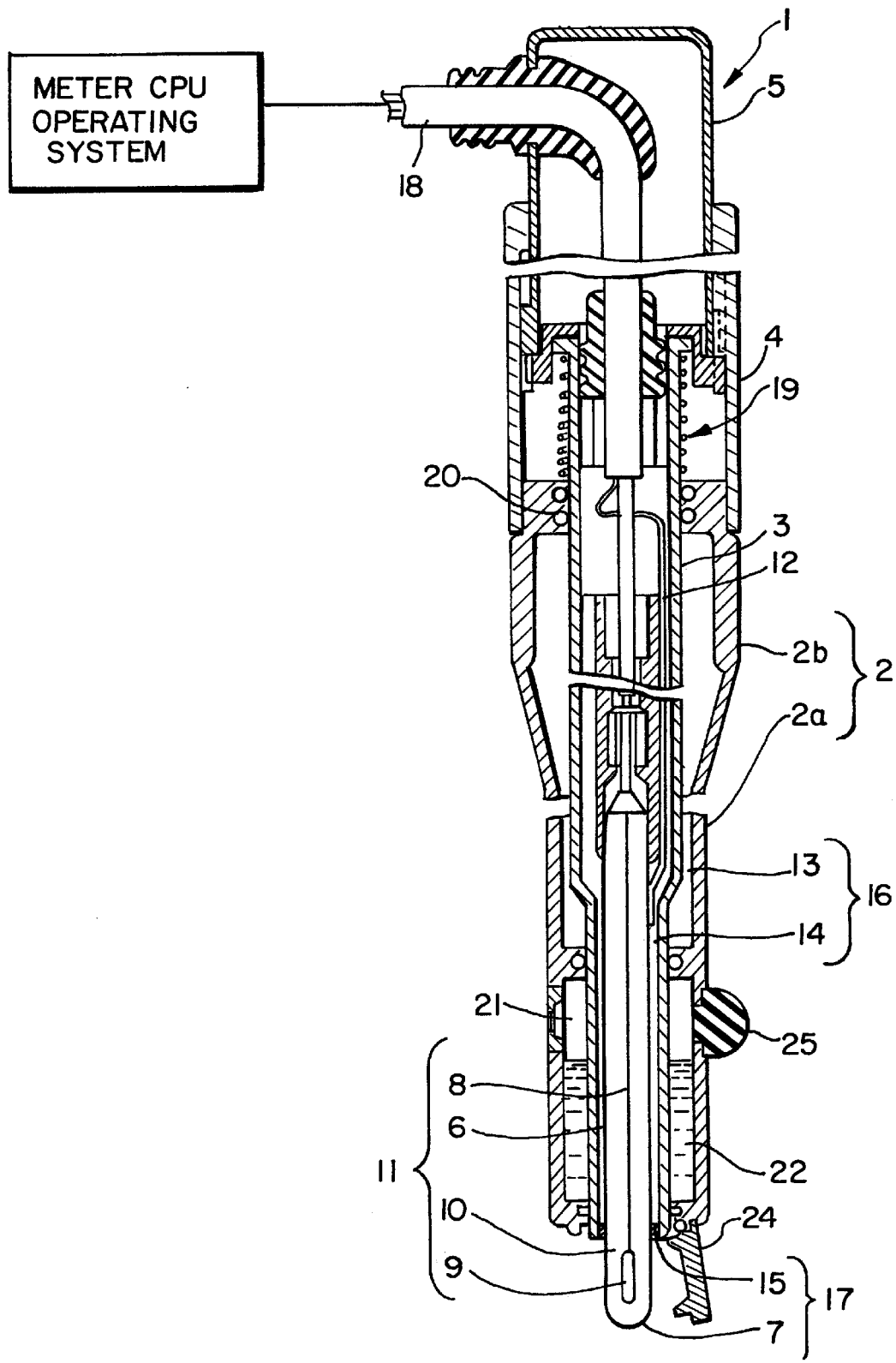
FIG. 1 is a partially segmented cross-sectional schematic of an ion concentration measuring apparatus of the first embodiment.

Referring to FIGS. 1 and 2, schematic illustrations of a pH meter as an ion concentration measuring apparatus representing a first embodiment of the present invention are disclosed. In FIG. 1, the pH meter 1 includes an elongated cylindrical body or housing member 2, with an upper and a lower opening, which movingly supports a measuring portion holder or measuring electrode assembly 3 so that it can move vertically along the axial direction of the housing. The housing body includes a mounting or sealing cap 4 that can be attached to an upper tube $2_b$ and a slightly reduced diameter lower tube $2_a$. The tube portions $2_a$ and $2_b$ can be formed from a synthetic plastic resin such as a hard vinyl chloride material. Subsequently, the sealing cap 4 can be mounted on the upper tube $2_b$ to support a retraction mechanism that will be subsequently described. The electrode measuring assembly 3 includes an inner measuring electrode tube 6 having a tip end 7 that can be formed into a pH responding portion such as a glass responding membrane. As can be appreciated, the present invention is not limited to a pH measuring instrument. Mounted within the measuring electrode inner tube 6 is an inner electrode 9 attached to a lead wire 8, which can provide output signals through the cable 18. An inner liquid 10 is filled to form the measuring electrode 11.

Between the measuring portion holder 3 and the measuring electrode inner tube 6 an inner reference electrode 13 is mounted at the tip end of the lead wire 12. At the same time, a gel formed reference electrode inner liquid 14 is provided to surround the measuring electrode inner tube 6 so that the gap with the measuring electrode inner tube 6 at the tip end of the measuring portion holder 3 provides a liquid junction 15, to thereby constitute a reference electrode 16. The measuring electrode assembly includes the pH responding portion 7 and the reference electrode 16. Thus the tip end side of the measuring portion holder 3 constitutes a measuring portion 17 which can be extended from the housing as shown in FIG. 1 so that the pH responding portion 7 of the measuring electrode 11 and the liquid junction 15 of the reference electrode 16 can be exposed to the exterior of the housing assembly. The wires attached to these respective electrodes can extend in a flexible cable 18 to a meter CPU operating system that is capable of providing not only output signals to be displayed to the operator, but also conducting an automatic calibration, as will be subsequently described.

As noted above, the construction of the measuring electrode assembly, per se, is essentially the same as a conventional pH meter.

Figure 12:
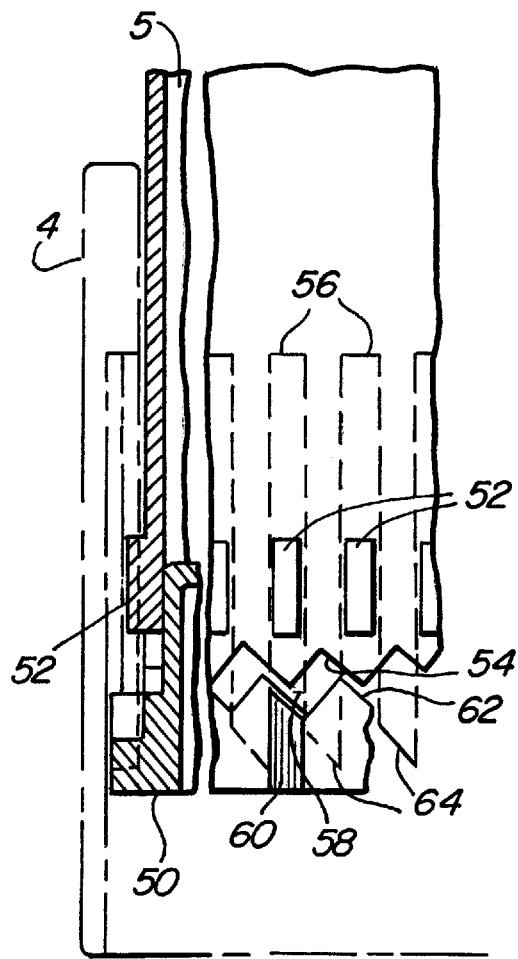
FIG. 12 is a partial cross-sectional view of the locking member being locked.

The upper portion of the housing member includes a retraction mechanism 19 that is similar to that employed in retractable mechanical pencils or ball point pens. That is, a spring 20 can bias a movable control member 5 so that it can be releasably locked in a retracted position, for example, as shown in FIG. 2b and FIG. 12, by simply the movement of the thumb or finger of an operator. A subsequent depression of the control member 5 will release its retention and permit it to be expanded outward from the housing member 2 to enable a storage mode of operation. Appropriate camming fingers can sequentially release and lock the control member 5 as the operator depresses the control member. Thus, pressing the head of the upper part of the control member 5 downward will change a condition from a nonmeasuring storage condition in FIG. 2b to the condition shown in FIG. 2a of a measurement enabling condition. In addition, subsequently pressing the head of the upper part of control member 5 downward as in FIG. 2a will change the condition of FIG. 2a to the condition shown in FIG. 2b. Thus, the present invention is designed to permit the measuring electrode assembly to travel freely back and forth in the axial direction with only a touch of a finger of the operator. As shown in FIG. 1, the spring 20 can be a helically wound spring that extends around the measuring portion holder 3, and can be seated within a locking member at the lower end of the control member 5. The spring 20 will bias the control member 5 and the electrode measuring apparatus towards a storage position.

Figure 11:
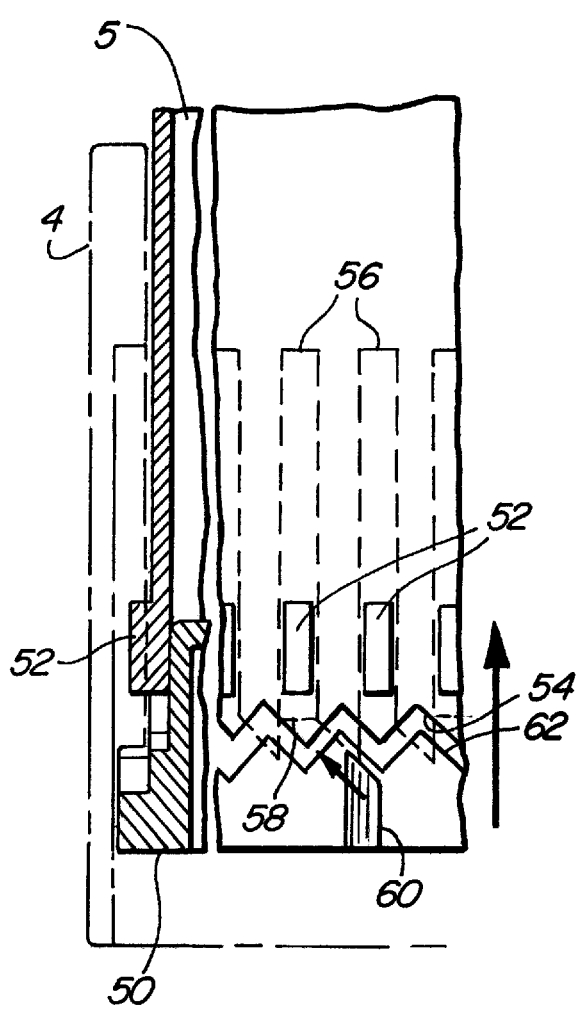
FIG. 11 is a cross-sectional view of the retention mechanism entering a locking mode.

Referring to FIG. 5, an exploded view of the retention mechanism 19 is disclosed with the control member 5 having a series of guide members 52 extending outward adjacent a set of saw tooth cam members 54 positioned at the lower surface of the control member 5. The guide members 52 are designed to fit within rectangular alignment grooves 56 within the mounting cap 4 to ensure an axial movement to the control member 5, see FIGS. 6, 7, and 8. The locking member 50 has complementary cam follower surfaces 56 that are adapted to be rotated in the clockwise direction by coaction with the cam surfaces 54 on the mounting cap 5. The locking member is biased upward, as can be seen in FIG. 1, by the spring 20. The locking member 50 rotates on the end of the measuring portion holder 3 when it is appropriately released from stops 58 within the mounting cap 4. The downward movement of the control member 5 along the axial direction causes the cam members 54 to force the locking member 50 downward so that its cam and guide member 60 are likewise moved downward in the axial direction by interaction with the rectangular grooves 56 within the mounting cap 4, as seen in FIG. 9. When the locking member 50 has been driven sufficiently downward so that its camming and guide member 60 is released from the grooves 56, see FIG. 10, then the camming surface 54 of the control member 5 will cause a rotation of the locking member 50, thereby permitting an engagement of the camming and guide member 60 with the lower cam surface 64 of the mounting cap member 4. This will cause the locking member to traverse to a locking position within the stop 58, see FIGS. 11 and 12. This, in turn, will hold the measuring portion holder 3 in an extended position so that the measuring electrode assembly 17 is cantilevered out of the housing member 2. This position is shown in FIG. 12 of the drawings. As subsequent depression of the control member 5 will enable the camming and guide member 60 of the locking member 50 to be released from the stop 58 and then to be subsequently cammed and rotated to an open groove 56 so that the measuring portion holder 3 will then be subject to the action of the spring 20 and be retracted into the housing member 2 for a storage and calibration mode of operation.

Referring to FIG. 2a, the lower portion of the housing cylindrical body 2 includes a calibrating fluid reservoir cavity 21 that surrounds the reference electrode. The calibration liquid 22, capable of calibrating the measuring portion 17 of the electrode measuring assembly, is stored within the housing body 2. The aperture 23 at the lower end of the housing body 2 can be sealed by a resilient lid 24 that can block the bottom opening 23 of the housing body 2 when the measuring portion holder 3 houses the measuring electrode assembly 17 completely within the body, as shown in FIG. 2b. This resilient lid 24 is pivotally mounted to open or close freely under the control of the operator. In addition, the aperture 23 is also formed to provide a liquid-tight sealing contact with the peripheral surface of the measuring portion holder 3 when the measuring portion holder 3 has its electrodes 17 protruding outside the body 2 in a measurement operating mode of operation as shown in FIG. 2a. Thus an operator can invert the measuring instrument, open the pivotable lid 24, and activate the control member 5 to extend the measuring electrode 17. In the extended position, the peripheral surface of the measuring portion holder 3 will seal, for example, around an annular sealing gasket as shown at the bottom of FIG. 1. The measuring instrument can then be held at any orientation relative to a sample surface for the measuring mode of operation.

An inversion of the instrument to retain the calibrating fluid within the reservoir 21 and a subsequent depression of the control member 5 will enable the electrodes 17 to be reinserted within the calibrating reservoir. A subsequent closing of the flexible sealing pivot lid 24 will retain the calibrating fluid and enable both the storage and/or calibrating mode of operation. The calibration liquid 22, for example, can be a proper pH standard solution as known in the art. It can be inserted through a port on the side of the lower portion of the housing member with a sealing stopper 25 used to seal the injection port.

Thus, the pH meter of the present invention is capable of retracting the entire measuring portion holder 3 into the body as shown in FIG. 2b during a nonmeasuring period, to thereby store the measuring electrodes 17 that are mounted at the top end of the measuring portion holder 3. In this condition the pH responding portion 7 of the measuring electrode portion 17 is protected and, at the same time, the pH responding portion 7 is immersed in the calibrating liquid 22 stored in the body within the housing 2, thereby enabling an automatic calibration of the measuring portion 17 by a meter CPU operating system.

In the measuring mode, the upper control member 5 can be activated downward in the axial direction so that it can protrude the measuring electrode portion 17 outside the housing body 2. This position is temporarily locked by the retraction mechanism 19, thereby enabling a measurement of the sample to determine a specific pH value. If the calibration of the instrument needs to be checked, again manipulating the control member 5 can retract the measuring electrode portion 17 to the inside portion of the body 2. In accordance with this configuration, the measuring electrode portion 17 can be immersed in the calibration liquid 22 to enable a desired calibration.

Figure 3A:
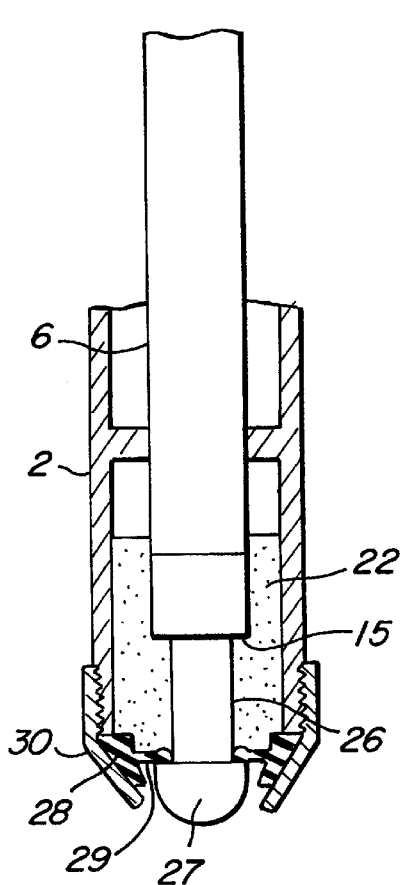
FIG. 3a is a partial schematic cross-sectional representation of a second embodiment of an ion concentration measuring apparatus in a storage and/or calibration mode.
Figure 3B:
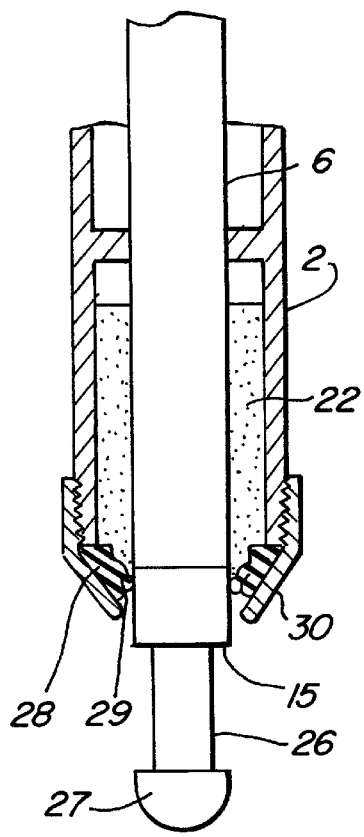
FIG. 3b is a partial schematic cross-sectional representation of an ion concentration measuring apparatus in an operative measuring mode.
Figure 4:
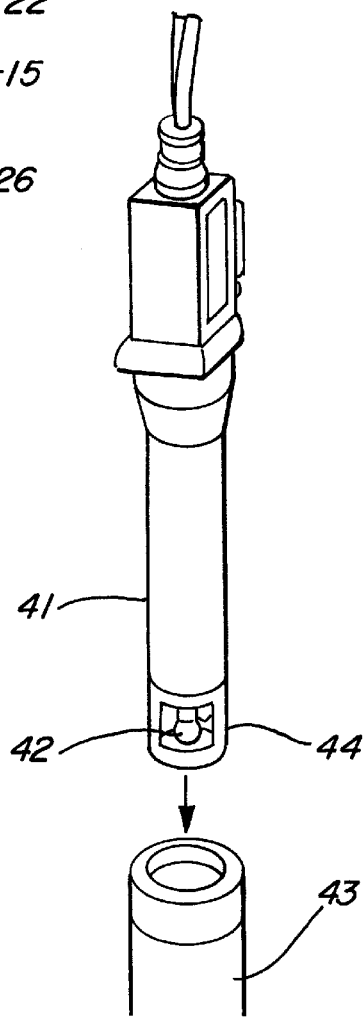
FIG. 4 is a perspective view of a conventional ion concentration measuring apparatus.

Referring to FIG. 3a and FIG. 3b, a second embodiment of the invention is disclosed. In this embodiment, the same retraction mechanism and an operator control member 5 are utilized. However, the lower portion of the housing body has been modified and the reference electrodes 15 and 7 of the first embodiment have been altered. The pH responding portion 26 is formed throughout the entire circumference of the side of the top end 6a of the measuring electrode inner tube 6. At its bottom end, for example, a rubber cap 27 is attached. Additionally, the lower opening of the housing body 2 includes a rubber bushing member 28 designed for sealing contact with a sealing portion 29 designed to provide a liquid-tight sealing contact with the pH responding portion 26. The rubber bushing 28 is maintained within a bushing retainer 30 that can be screwed onto helical threads at the lower end of the housing. As can be appreciated from FIG. 3a, the rubber cap 27 can facilitate both protecting and sealing the electrode measuring portion within the cavity containing the calibrating liquid 22. In this design, the electrode portion 6 can be inserted and extracted while maintaining a sealing contact to retain the calibrating fluid 22. As can be appreciated, although not shown, a port can be provided for adding and subtracting calibrating fluid, and also to permit a rinsing or washing of the interior of the cavity and the electrode. If the sample is not particularly contaminating, the calibrating fluid 22 can be repetitively used.

The present invention is not limited to the above-mentioned embodiments, and various modifications can be implemented. For example, pH responding portions 7 and 26 may be constructed using an ISFET other than glass membranes. The liquid junction 15 of the reference electrode 16 may also be constructed in a so-called junction system.

As can be readily appreciated, the small hand-held sensor for a pH measuring instrument, calcium ion concentration meter, or potassium ion concentration meter can advantageously incorporate the ability to movably mount the measuring portion so that it can extend either exterior of the housing body in a measuring mode of operation, or can be retracted for both a storage and a calibration mode of operation, with the operator simply manipulating a control member at one end of the sensor. The housing body incorporates a reservoir of calibration liquid that is stored at the interior portion of the housing body adjacent an opening tip for the measuring portion of the holder. Appropriate seals can be used to ensure a liquid-tight retention of the calibration fluid.

Thus, the measuring portion of the sensor can be reliably protected and can be automatically calibrated when measurement is not carried out. At the same time, the measurement condition can be changed over to a nonmeasurement condition simply by the touch of a finger by the operator. Calibration can be carried out easily as required during measurement, and an ion concentration measuring apparatus with superb maneuverability can be obtained.

Those skilled in the art will appreciate that various adaptations and modifications of the just-described preferred embodiment can be configured without departing from the scope and spirit of the invention. Therefore, it is to be understood that, within the scope of the appended claims, the invention may be practiced other than as specifically described herein.

What is claimed is:

1. An ion concentration measuring apparatus comprising:
    a housing member;
    a measuring electrode assembly including a pH responding portion and a liquid junction movably mounted within the housing member for measuring ion concentration;
    means for moving the measuring electrode assembly so that the measuring electrode assembly can be stored within the housing member or extended from the housing member and includes a control member mounted to movably extend from an upper end of the housing member and to move in an axial direction and to be operatively connected to the measuring electrode assembly and means for releasably holding the control member at a retracted position within the housing member to fixedly maintain the measuring electrode assembly at an extended measuring mode of operation outside of the housing member and releasing the control member to permit the control member to project outward from the housing member and correspondingly retract the measuring electrode assembly to enable calibration in a storage position;
    means within the housing member for enabling calibration of the measuring electrode assembly when the measuring electrode assembly is stored within the housing member including a reference electrode and a calibration liquid reservoir with a reference electrode liquid; and:
    means for sealing the measuring electrode assembly so that the measuring electrode assembly is within the housing member, to prevent release of the reference electrode liquid when the means for moving moves the measuring electrode assembly in the axial direction from the storage position to an extended position.

2. The invention of claim 1 wherein the means for sealing includes a pivoting seal member mounted at the lower end of the housing number.

3. The invention of claim 1 wherein the measuring electrode assembly is cylindrical in shape and the sealing means includes a sealing cap member mounted on a lower end of the measuring electrode assembly member.

4. The invention of claim 3 wherein the lower end of the housing member includes an annular flexible sealing ring mounted within the housing member adjacent the aperture.

5. An ion concentration measuring apparatus comprising:
    a hollow elongated housing member configured to be hand-held by an operator with an upper opening and a lower opening;
    an elongated electrode measuring member having, at a lower end, a measuring electrode and a reference electrode for measuring ion concentration;
    means for storing a calibration fluid within the housing member;
    means for movably mounting the electrode measuring member in the housing member to enable the measuring electrode and reference electrode to be positioned in a measuring mode to measure ion concentration exterior of the housing member and in a storage and calibrating mode in the interior of the housing member, including a control member, having a predetermined range of movement, extending through the upper opening and operatively connected to the elongated electrode measuring member;
    means for resiliently biasing the control member towards an extension position to thereby extend above the upper opening adjacent one end of the range of movement, and means for releasably holding the control member in a retracted position adjacent the other end of the range of movement, whereby the operation of the control member by an operator to the retracted position will move the electrode measuring member to the measuring mode and the subsequent release of the control member will move the electrode measuring member to the storage and calibrating mode;
    means within the housing member for enabling calibration of the electrode measuring member when the electrode measuring member is stored within the housing member including the calibration fluid; and
    means for sealing the electrode measuring member, so that the measuring electrode assembly is within the housing member, to prevent leakage of the calibration fluid from the housing member during movement of the electrode measuring member.

6. The invention of claim 5 wherein the means for movably mounting includes a locking member and camming means mounted on the control member for releasing and rotating the locking member from sequentially a lock position and a release position.

\* \* \* \* \*